United States Patent [19]

Gayer et al.

[11] Patent Number: 5,196,541
[45] Date of Patent: Mar. 23, 1993

[54] PROCESS FOR THE PREPARATION OF SUBSTITUTED 3-AMINOACRYLIC ESTERS

[75] Inventors: Herbert Gayer, Monheim-Baumberg; Alexander Klausener, Krefeld; Peter C. Knüppel, Wermelskirchen, all of Fed. Rep. of Germany; Fritz Maurer, Yuki, Japan

[73] Assignee: Bayer Aktiengesellschaft, Leverkusen, Fed. Rep. of Germany

[21] Appl. No.: 739,746

[22] Filed: Aug. 2, 1991

[30] Foreign Application Priority Data

Aug. 16, 1990 [DE] Fed. Rep. of Germany ....... 4025892

[51] Int. Cl.$^5$ ............... C07D 261/14; C07D 277/38; C07D 229/34; C07D 227/10; C07D 231/38
[52] U.S. Cl. .................. 546/312; 560/62; 560/100; 560/103; 560/121; 560/123; 560/124; 560/17; 560/43; 560/61; 560/.1; 540/288; 540/289; 540/296; 540/297; 546/300; 546/307; 546/310; 548/183; 548/184; 548/190; 548/191; 548/194; 548/243; 548/244; 548/245; 548/246; 548/247; 548/375.1; 548/484; 548/485; 548/486; 548/306.1; 548/307.1; 548/306.4; 548/.7; 548/309.7; 548/314.7; 548/324.1; 548/326.1; 548/362.5; 548/364.1; 548/370.1; 548/371.7; 548/337.1; 548/328.5
[58] Field of Search ............... 546/312, 288, 289, 296, 546/297, 300, 307, 310; 548/183, 184, 190, 191, 194, 243, 244, 245, 246, 247, 375, 376, 378, 484, 485, 486; 560/1, 17, 43, 61, 62, 100, 103, 121, 123, 124

[56] References Cited

U.S. PATENT DOCUMENTS 4,968,709 11/1990 Kleefeld et al. ................ 546/270
5,036,085 7/1991 Heinemann et al. ............. 548/128

OTHER PUBLICATIONS

Chemical Abstracts, vol. 114, No. (9) Abstrast 81,601u, Mar. 4, 1991, Klausener et al.

*Primary Examiner*—C. Warren Ivy
*Assistant Examiner*—Zinna N. Davis
*Attorney, Agent, or Firm*—Sprung Horn Kramer & Woods

[57] ABSTRACT

There is described a new process for the preparation of substituted 3-aminoacrylic esters of the general formula (I)

$$R^1-(X)_n\underset{\underset{\underset{R^4}{|}}{\underset{N-R^3}{\diagdown}}}{\overset{COOR^2}{\overset{\diagup}{\underset{CH}{\overset{\|}{C}}}}} \quad (I)$$

in which
$R^1, R^2, R^3, R^4$, X and n have the meaning given in the description.

The 3-aminoacrylic esters of the formula (I) are obtained by reacting acetic esters of the formula (II)

$$R^1-(X)_n-CH_2-COOR^2 \quad (II)$$

with orthoformic acid diamide esters of the formula (III)

$$R^9-\underset{\underset{R^{10}}{|}}{\overset{\overset{R^8}{|}}{C}}-O-CH\underset{\underset{\underset{R^4}{|}}{N-R^3}}{\overset{\overset{R^4}{|}}{\diagdown}}\underset{N-R^3}{\diagup} \quad (III)$$

5 Claims, No Drawings

PROCESS FOR THE PREPARATION OF SUBSTITUTED 3-AMINOACRYLIC ESTERS

The invention relates to a new process for the preparation of substituted 3-aminoacrylic esters which can be used as fungicides or as intermediates for the preparation of fungicidal alkoxyacrylic esters.

It has been disclosed that certain fungicidally active alkoxyacrylic esters are obtained when suitable acetic ester derivatives are condensed with formic ester derivatives in the presence of a base, and, in a second step, the resulting 3-hydroxyacrylic ester derivatives are then alkylated on the 3-hydroxyl group using alkylating agents in the presence of a base (cf., for example, DE-OS (German Published Specification) 3,805,059; DE-OS (German Published Specification) 3,807,232).

The disadvantage of this process consists in the fact that the Claisen condensation, which is carried out as the first step, often gives only very poor yields and does not work at all in the case of some acetic ester derivatives, depending on the nature of the substituent in the 2-position.

Furthermore, it has been disclosed that fungicidally active substituted 3-aminoacrylic esters are obtained when suitable acetic ester derivatives are reacted with formamides or formamide derivatives (cf., for example, DE-OS (German Published Specification) 3,807,232; DE-OS (German Published Specification) 3,910,358). However, the dimethylformamide dialkyl acetals which are used in this process also frequently only provide very poor yields of the desired end product.

It has now been found that substituted 3-aminoacrylic esters of the general formula (I)

$$R^1-(X)_n\diagdown_C\diagup^{COOR^2}$$
$$\|$$
$$CH$$
$$|$$
$$N-R^3$$
$$|$$
$$R^4$$

(I)

in which $R^1$ represents a carbo- or heterocycle, each of which is optionally substituted, $R^2$ represents optionally substituted alkyl, $R^3$ and $R^4$ either independently of one another in each case represent optionally substituted alkyl, or together with the nitrogen atom to which they are bonded represent an optionally substituted heterocycle which can optionally contain further hetero atoms, X represents oxygen, sulphur or one of the radicals $$-C-\quad\text{or}\quad-N-$$
$$R^5\diagup\diagdown R^6\qquad\quad R^7$$

and n represents a number 0 or 1, where $R^5$, $R^6$ and $R^7$ independently of one another in each case represent hydrogen or represent alkyl or alkenyl, each of which is optionally substituted, are obtained when substituted acetic esters of the formula (II)

$$R^1-(X)_n-CH_2-COOR^2 \qquad (II)$$

in which $R^1$, $R^2$, X and n have the abovementioned meaning, are reacted with orthoformic acid diamide esters of the formula (III)

$$R^8\qquad\quad R^4$$
$$|\qquad\quad\;\;|$$
$$R^9-C-O-CH\diagup^{N-R^3}$$
$$|\qquad\qquad\diagdown_{N-R^3}$$
$$R^{10}\qquad\qquad\;\;|$$
$$\qquad\qquad\qquad R^4$$

(III)

in which $R^8$ represents hydrogen or alkyl, $R^9$ and $R^{10}$ either independently of one another in each case represent alkyl, or together with the carbon atom to which they are bonded represent a cycloalkyl radical, and $R^3$ and $R^4$ have the abovementioned meaning,
if appropriate in the presence of a diluent.

In this context, it is especially surprising that the reaction, with orthoformic acid diamide esters, according to the invention gives high yields of the desired end products since the reactions with similarly reactive dimethylformamide dialkyl acetals are impossible to carry out in many cases.

It is therefore a particular advantage of the process according to the invention that, by applying it, compounds are accessible which could previously not be obtained at all, or only in very poor yields.

It is a further advantage of the process according to the invention that the substituted 3-aminoacrylic esters which can be obtained with ease and in high yields with the aid of the process according to the invention are also suitable as intermediates for of fungicidal 3-alkoxyacrylic esters when the 3-amino group is hydrolysed under acid conditions and the resulting 3-hydroxyacrylic esters are alkylated either in a second separate reaction step or directly afterwards in a one-pot process. The 3-alkoxyacrylic esters, which are valuable as fungicides in plant protection, can therefore be prepared with greater ease and in better yields than by using the known processes.

Formula (I) provides a general definition of the substituted 3-aminoacrylic esters which can be obtained with the aid of the process according to the invention. Compounds of the general formula (I) which can preferably be prepared are those in which $R^1$ represents a carbocycle which has 5 to 10 carbon atoms and which is optionally monosubstituted or polysubstituted by identical or different substituents, saturated, monounsaturated or polyunsaturated or aromatic, or represents a heterocycle which has 2 to 9 carbon atoms and 1 to 5 identical or different hetero atoms—in particular nitrogen, oxygen or sulphur—and which is optionally monosubstituted or polysubstituted by identical or different substituents, saturated, monounsaturated or polyunsaturated or aromatic, suitable substituents in each case being: halogen, cyano, nitro, in each case straight-chain or branched alkyl, alkoxy or alkylthio, each of which has 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl, alkoximinoalkyl, dialkylamino or dialkylaminocarbonyl, each of which has 1 to 4 carbon atoms in the individual alkyl moieties, in each case straight-chain or branched alkenyl or alkinyl, each of which has 2 to 8 carbon atoms, cycloalkyl having 3 to 7 carbon atoms, divalent alkanediyl having 3 to 5 carbon atoms, or aryl, aryloxy, arylthio, arylcarbonyl, aralkyl, aralkenyl, aralkinyl, aralkyloxy, aralkylthio, heteroarylalkyl, heteroarylalkenyl, heteroaryloxy, heteroarylthio, heteroarylcarbonyl, heteroary;alkyloxy, heteroarylalkylthio or heteroaryl, each of which has 6 to 10 carbon atoms in the aryl moiety or 2 to 9 carbon atoms and 1 to 4 identical or different hetero atoms—in particular nitrogen, oxygen and/or sulphur—in the heteroaryl moiety and if appropriate 1 to 6 carbon atoms in the straight-chain or branched alkyl moiety or if appropriate 2 to 6 carbon atoms in the straight-chain or branched alkenyl moiety or alkinyl moiety, each of which is optionally monosubstituted or polysubstituted in the aryl moiety or in the heteroaryl moiety by identical or different substituents from the series comprising halogen, alkyl, alkoxy, alkylthio, halogenoalkyl, halogenoalkoxy, halogenoalkylthio, dioxyalkylene, halogen-substituted dioxyalkylene or optionally substituted phenyl;

$R^2$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted or polysubstituted in the aryl moiety by identical or different substituents, suitable aryl substituents being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, or aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms, or heteroarylalkyl or heteroaryl, each of which has 2 to 9 carbon atoms and 1 to 4 identical or different hetero atoms,—in particular nitrogen, oxygen and/or sulphur—in the heteroaryl moiety and if appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms;

$R^3$ and $R^4$ either independently of one another in each case represent straight-chain or branched alkyl having 1 to 6 carbon atoms, or together with the nitrogen atom to which they are bonded represent a saturated 5- to 7-membered heterocycle which can optionally contain a further hetero atom—in particular nitrogen, oxygen or sulphur—and which is optionally monosubstituted or polysubstituted by identical or different substituents, suitable substituents being straight-chain or branched alkyl radicals having 1 to 4 carbon atoms, X represents oxygen, sulphur or one of the radicals

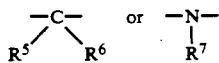

and n represents a number 0 or 1 where $R^5$, $R^6$ and $R^7$ independently of one another in each case represent hydrogen, in each case straight-chain or branched alkyl having 1 to 6 carbon atoms or alkenyl having 2 to 6 carbon atoms, or represent aralkyl which has 1 to 6 carbon atoms in the straight-chain or branched alkyl moiety and 6 to 10 carbon atoms in the aryl moiety or aralkenyl which has 2 to 6 carbon atoms in the straight-chain or branched alkenyl moiety and 6 to 10 carbon atoms in the aryl moiety, each of these aralkyl or aralkenyl radicals optionally being monosubstituted or polysubstituted in the aryl moiety by identical or different substituents, suitable aryl substituents in each case being those mentioned in the case of $R^2$.

Compounds of the formula (I) which can particularly preferably be prepared are those in which $R^1$ represents a phenyl radical which is optionally monosubstituted to pentasubstituted by identical or different substituents and/or benzo-fused, or represents a cycloalkenyl radical which has 5 to 7 carbon atoms and which is optionally monosubstituted to pentasubstituted by identical or different substituents, or represents a heteroaryl radical which has 1 to 5 carbon atoms and 1 to 3 hetero atoms—in particular nitrogen, oxygen or sulphur—and which is optionally monosubstituted to pentasubstituted by identical or different substituents and/or benzo-fused, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl,ethoximinoethyl,dimethylamino, diethylamino, dimethylcarbamoyl, diethylcarbamoyl, allyl, butenyl or propargyl, cyclopropyl, cyclopentyl, cyclohexyl, 1,3-propanediyl, 1,4-butanediyl, 1,5-pentanediyl, or phenyl, naphthyl, phenoxy, phenylthio, phenylcarbonyl, benzyl, phenylethyl, phenylpropyl, phenylethenyl, benzyloxy, heteroaryloxy, heteroarylmethyl or heteroaryl, each of which is optionally monosubstituted to trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy, trifluoromethylthio, dioxymethylene or phenyl which is optionally monosubstituted to trisubstituted by identical or different substituents from the series comprising fluorine, chlorine, methyl, methoxy or trifluoromethyl, suitable individual heteroaryl radicals in each case being the following:

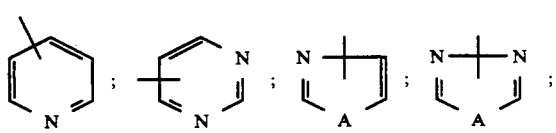

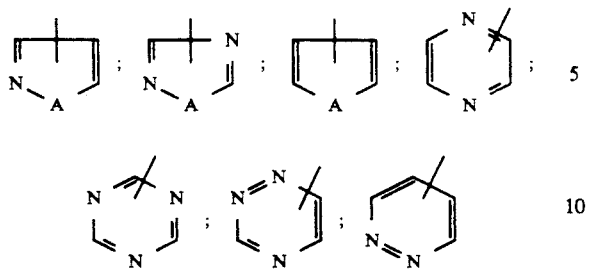

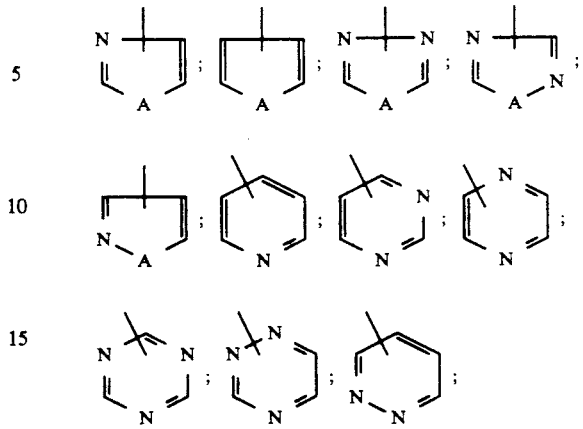

which can optionally also be benzo-fused and in which

A in each case represents oxygen, sulphur or an NH group;

R² represents methyl, ethyl, n- or i-propyl, n-, i-, s- or t-butyl, or represents benzyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl,ethoximinomethyl,methoximinoethyl, ethoximinoethyl, cyclopentyl, cyclohexyl, 1,3-propanediyl, 1,4-butanediyl, or phenyl, benzyl, phenoxy or benzyloxy, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, R³ and R⁴ either independently of one another in each case represent methyl, ethyl, n- or i-propyl, or n-, i-, s- or t-butyl, or together with the nitrogen atom to which they are bonded represent a 1-pyrrolidinyl, 1-piperidinyl or 4-morpholinyl radical, X represents oxygen, sulphur or one of the radicals

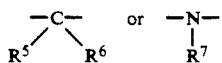

and n represents a number 0 or 1, where

R⁵, R⁶ and R⁷ independently of one another in each case represents hydrogen, methyl, ethyl, n- or i-propyl or n-, i-, s- or t-butyl, or represents benzyl or phenyl, each of which is optionally monosubstituted to trisubstituted by identical or different substituents, suitable substituents in each case being those mentioned in the case of R².

Compounds of the general formula (I) which can very particularly preferably be prepared are those in which R¹ represents a phenyl radical which is optionally monosubstituted to trisubstituted and/or benzofused, or represents a cyclohexenyl radical or cyclopentenyl radical, each of which is optionally monosubstituted to trisubstituted by identical or different substituents and/or benzo-fused, or represents a heteroaryl radical which is optionally monosubstituted to trisubstituted and/or benzo-fused, particularly suitable heteroaryl radicals being:

where

A in each represents oxygen, sulphur or an NH group and where the following are in each case suitable as phenyl, cyclopentenyl, cyclohexenyl or heteroaryl substituents: fluorine, chlorine, bromine, cyano, nitro, methyl, ethyl, methoxy, methylthio, trifluoromethyl, trifluoromethoxy, trifluoromethylthio, methoxycarbonyl, ethoxycarbonyl, dimethylamino, or phenyl, phenoxy, phenylcarbonyl, benzyl, pyridyl, pyrazolyl, oxazolyl, thiazolyl, thienyl, furyl, thiadiazolyl, oxadiazolyl, imidazolyl or triazolyl, each of which is optionally monosubstituted to trisubstituted by identical or different substituents from the series comprising fluorine, chlorine, methyl, ethyl, methoxy, trifluoromethyl, dioxymethylene or phenyl and/or benzo-fused, R² represents methyl, ethyl, n- or i-propyl or benzyl, R³ and R⁴ in each case represent methyl or ethyl, X represents oxygen, sulphur or one of the radicals

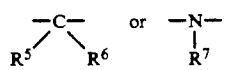

and n represents a number 0 or 1, where R⁵, R⁶ and R⁷ independently of one another in each case represent hydrogen, methyl, ethyl, n- or i-propyl or benzyl.

Aryl as such or in composite radicals denotes phenyl or naphthyl, in particular phenyl.

All aliphatic radicals as such or in composite radicals are straight-chain or branched.

Unless otherwise defined, halogen represents fluorine, chlorine, bromine or iodine, in particular fluorine, chlorine or bromine.

If, for example, methyl N-methyl-N-[2-(6-phenyl)-pyridyl]-glycinate and 1,1-bis-[dimethylamino]-methyl t-butyl ether are used as starting substances, then the course of the reaction of the process according to the invention may be described by the following equation:

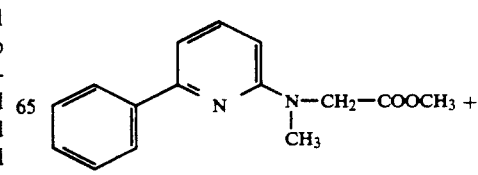

-continued

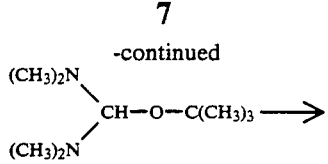

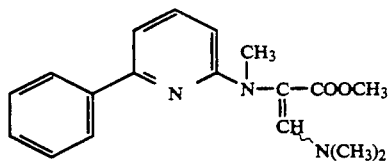

Formula (II) provides a general definition of the substituted acetic esters required as starting substances for carrying out the process according to the invention. In this formula (II), $R^1$, $R^2$, X and n preferably represent those radicals which have already been mentioned in connection with the description of the substances of the formula (I) according to the invention as being preferred for these substituents.

The substituted acetic esters of the formula (II) are known or can be obtained in analogy to known processes (cf., for example, J. Chem. Pharm. Bull. 23, 3008-3010 [1975]; Prakt. Chem. 315, 1175-1182 [1973]; Chimia 28, 235-236 [1974]; Pak. J. Sci. Ind. Res. 20, 139-149 [1977]; J. Heterocycl. Chem. 5, 281-283 [1968]; Pol. J. Chem. 53, 2349-2354 [1979]; J. Heterocycl. Chem. 24, 85-89 [1987]; Zh. org. Khim. 20, 1517-1538 [1984]; Zh. Org. Khim. 20, 2002-2011 [1984]; Izv. Akad. Nauk SSSR. Ser. Khim. 1984, 2760-2765; DE 2,103,728; DE 2,637,911; DE 2,709,108; DE 2,725,361; DE 2,425,282; GB 1,161,492 [1969]; EP 182,769; EP 245,230; EP 227,932; DE-OS (German Published Specification) 3,904,931; DE-OS (German Published Specification) 3,805,059; DE-OS (German Published Specification) 3,807,232; DE-OS (German Published Specification) 3,905,119; DE-OS (German Published Specification) 3,904,931).

Formula (III) provides a general definition of the orthoformic acid diamide esters furthermore required as starting substances for carrying out the process according to the invention. In this formula (III), $R^3$ and $R^4$ preferably represent those radicals which have already been mentioned in connection with the description of the substances of the formula (I) according to the invention as being preferred for these substituents $R^8$ preferably represents hydrogen or straight-chain or branched alkyl having 1 to 4 carbon atoms, particularly preferably hydrogen or methyl;

$R^9$ and $R^{10}$ preferably independently of one another in each case represent straight-chain or branched alkyl having 1 to 4 carbon atoms, or together with the carbon atom to which they are bonded represent cycloalkyl having 5 to 7 carbon atoms;

$R^9$ and $R^{10}$ particularly preferably represent methyl or ethyl or together with the carbon atom to which they are bonded represent a cyclohexyl radical.

The orthoformic acid diamide esters of the formula (III) are also known (cf., for example, Chem. Ber. 101, 41-50 [1968]; Chem. Ber. 101, 1885-1888 [1968]; DE 2,303,919; PCT Int. Appl. WO 8,601,204) or can be obtained in analogy to known processes.

Suitable diluents for carrying out the process according to the invention are inert organic solvents These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, amides such as dimethylformamide, dimethylacetamide, N-methylformanilide, N-methylpyrrolidone or hexamethylphosphoric triamide.

It is also possible to carry out the process according to the invention without adding any solvents at all.

When carrying out the process according to the invention, the reaction temperatures can be varied within a substantial range. In general, the process is carried out at temperatures from $-35°0$ C. to $+150°$ C., preferably at temperatures from 0° C. to 120° C.

The process according to the invention can also be carried out under reduced or increased pressure, but preferably under atmospheric pressure.

If appropriate, it can be expedient to use an inert gas atmosphere such as, for example, nitrogen or argon, but it is generally possible to carry out the process according to the invention under a normal room air atmosphere.

For carrying out the process according to the invention, 1.0 to 15.0 moles, preferably 1.0 to 5.0 moles, of orthoformic acid diamide ester of the formula (III) are generally employed per mole of substituted acetic ester of the formula (II). The reaction is carried out and the reaction products are worked up and isolated by generally customary methods (cf. also the preparation examples).

The substituted 3-aminoacrylic esters which can be prepared with the aid of the process according to the invention are fungicides which are known in some cases (cf., for example, DE-OS (German Published Specification) 3,904,931; DE-OS (German Published Specification) 3,905,119; DE-OS (German Published Specification) 3,807,232). The new 3-aminoacrylic esters are claimed in a parallel application.

In addition, they can be used as intermediates for the preparation of other known fungicides of the formula (IV)

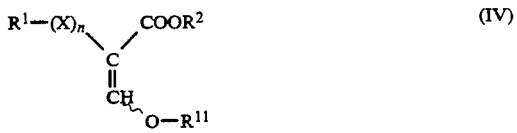

in which $R^{11}$ represents alkyl and $R^1$, $R^2$, X and n have the abovementioned meanings, (cf., for example, DE-OS (German Published Specification) 3,904,931; DE-OS (German Published Specification) 3,905,119; DE-OS (German Published Specification) 3,807,232), by first hydrolysing the amino group in the 3-position in a customary fashion, for example using equimolar amounts of dilute hydrochloric acid at temperatures between 0° and 60° C., if appropriate in the presence of a diluent such as, for example, acetonitrile or dimethylformamide, in the course of four to eight hours (in the case of starting compounds of the formula (I) which contain several basic groups in the molecule, it is necessary to employ one equivalent of hydrochloric acid for each basic group), and subsequently alkylating the resulting substituted 3-hydroxyacrylic esters of the formula (V)

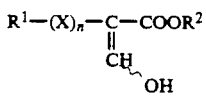 (V)

in which

R[1], R[2], X and n have the abovementioned meaning, either in a separate reaction step or in a one-pot process, also in a customary fashion, using alkylating agents such as, for example, dimethyl sulphate, if appropriate in the presence of a diluent such as, for example, dimethylformamide, and if appropriate in the presence of a reaction auxiliary such as, for example, potassium carbonate, at temperatures between −20° and +120° C.

PREPARATION EXAMPLES

EXAMPLE 1

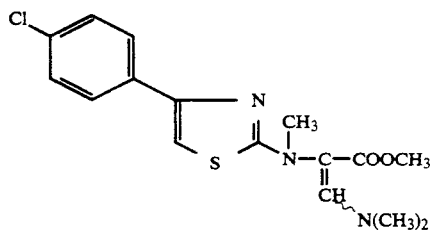

A mixture of 14.8 g (0.04987 mol) of methyl N-[4-(4-chlorophenyl)-thiazol-2-yl]-N-methylaminoacetate (preparation analogously to DE-OS (German Published Specification) 3,807,232) and 20 g (0.124 mol) of t-butyloxy-bis-(dimethyl-amino)-methane is heated for 12 hours at 100° C., subsequently cooled treated with 200 ml of water and 200 ml of ethyl acetate and stirred for 2 hours at room temperature, and crystals which have precipitated are filtered off with suction and dried. The ethyl acetate phase is evaporated, and the residue is suspended in diisopropyl ether, filtered off with suction and dried.

16.3 g (92.9% of theory) of methyl 2-{N-[4-(4-chlorophenyl)-thiazol-2-yl]-N-methyl-amino}-3-dimethylaminoacrylate of melting point 177°-178° C. are obtained (purity according to gas chromatography 99%).

EXAMPLE IV-1

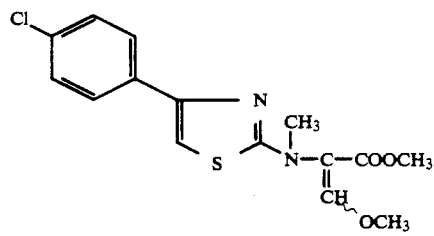

To 5.3 g (0.015 mol) of methyl 2-{N-[4-(4-chlorophenyl)thiazol-2-yl]-N-methylamino}-3-dimethylaminoacrylate in 20 ml of dimethylformamide there are added 15 ml (0.033 mol) of 2-normal aqueous hydrochloric acid, the mixture is heated for 4 hours at 60° C., cooled and poured into saturated aqueous ammonium chloride solution, and this is extracted with ethyl acetate. The organic phase is evaporated, the residue is dissolved in 30 ml of dimethylformamide 2.05 g (0.015 mol) of potassium carbonate and 3.05 g (0.023 mol) of dimethyl sulphate are added, and the mixture is stirred for 16 hours at room temperature. For working up, the reaction mixture is poured into water and extracted using ethyl acetate, the organic phase is dried over sodium sulphate and concentrated in vacuo, and the residue is chromatographed on silica gel (eluent: ethyl acetate/hexane).

4.6 g (90% of theory) of methyl 2-{N-[4-(4-chlorophenyl)thiazol-2-yl]-N-methylamino}-3-methoxyacrylate of melting point 104°-105° C. are obtained.

EXAMPLE 2

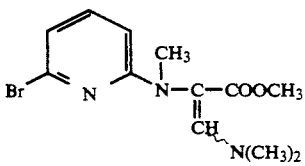

1.05 g (0.00405 mol) of methyl [N-(6-bromo-2-pyridyl)-N-methyl]-aminoacetate (cf., for example, DE-OS (German Published Specification) 3,904,931) and 1.05 g (0.00651 mol) of t-butyloxy-bis-(dimethylamino)-methane are refluxed for 18 hours in 10 ml of toluene. To complete the reaction, a further 0.5 g (0.0031 mol) of t-butyloxy-bis-(dimethylamino)-methane are added, the mixture is refluxed for another 2 hours and then cooled, water is added, and this mixture is stirred for 2 hours at room temperature. The organic phase is subsequently separated off, the aqueous phase is extracted using toluene, and the combined organic extracts are dried over sodium sulphate and concentrated.

1.15 g (90.4% of theory) of methyl 2-[N-(6-bromo-2-pyridyl)-N-methyl]-amino-3-dimethylaminoacrylate of melting point 106° C. are obtained (purity according to gas chromatography 90%).

EXAMPLE 3

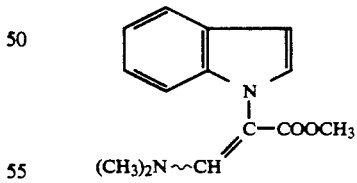

7.6 g (0.04 mol) of methyl 1-indolylacetate and 10.5 g (0.06 mol) of t-butyloxy-bis-(dimethylamino)-methane are heated for one hour at a bath temperature of 100° C. Volatile components are subsequently removed in vacuo, and the residue is chromatographed on silica gel (eluent: dichloromethane).

6.5 g (67% of theory) of methyl 3-dimethylamino-2-indolylacrylate are obtained as an oil.

$^1$H NMR (CDCl$_3$/tetramethylsilane): δ=6.57 (1H); 7.0 (1H); 7.1-7.2 (3H); 7.55-7.65 (1H); 7.7 (1H) ppm.

EXAMPLE 4

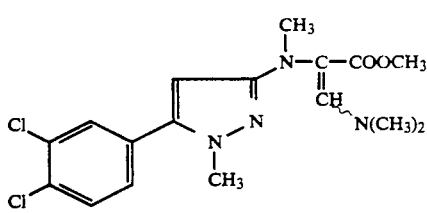

3.3 g (0.01 mol) of methyl N-[5-(3,4-dichlorophenyl)-1-methylpyrazol-3-yl]-N-methylaminoacetate are heated for one hour at a bath temperature of 100° C. together with 2.6 g (0.015 mol) of t-butoxy-bis-(dimethylamino)methane. The resulting reaction mixture is separated by chromatography on silica gel (eluent: ether/petroleum ether 1:3).

2.7 g (71% of theory) of methyl 2-{N-[5-(3,4-dichlorophenyl)-1-methyl-pyrazol-3-yl]-N-methylamino}-3-dimethylaminoacrylate of melting point 113°–114° C. are obtained.

EXAMPLE V-4

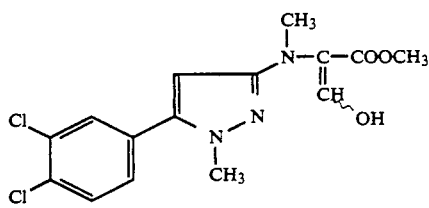

3 g (0.0078 mol) of methyl 2-{N-[5-(3,4-dichlorophenyl)-1-methylpyrazol-3-yl]-N-methylamino}-3-dimethylaminoacrylate and 4.3 ml (0.0086 mol) of 2-normal hydrochloric acid are heated for 6 hours at 60° C. For working-up, the reaction mixture is diluted with water and extracted with dichloromethane, the organic phase is dried over sodium sulphate and the solvent is subsequently removed in vacuo.

1.3 g (47% of theory) of methyl 2-{N-[5-(3,4-dichlorophenyl)-1-methyl-pyrazol-3-yl]-N-methylamino}-3-hydroxyacrylate are obtained as an oily crude product which can be employed in the next step without further purification.

EXAMPLE IV-4

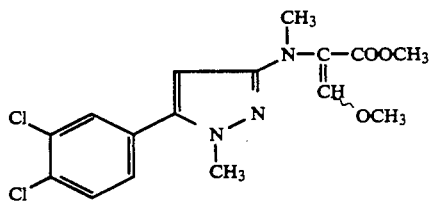

1.3 g (0.0036 mol) of methyl 2-{N-[5-(3,4-dichlorophenyl)-1-methylpyrazol-3-yl]-N-methylamino}-3-hydroxyacrylate and 1 g (0.0072 mol) of potassium carbonate are stirred for 16 hours at room temperature together with 0.51 g (0.004 mol) of dimethyl sulphate in 5 ml of dimethylformamide. For working-up, the mixture is concentrated in vacuo, the residue is partitioned between water and dichloromethane, the organic phase is separated off, dried and concentrated, and the residue is chromatographed on silica gel. (Eluent: dichloromethane/methanol 40:1).

0.9 g (67% of theory) of methyl 2-{N-[5-(3,4-dichlorophenyl)-1-methylpyrazol-3-yl]-N-methylamino}-methoxyacrylate is obtained as an oil.

$^1$H NMR (CDCl$_3$/tetramethylsilane): $\delta$=7.86 (1H); 7.57–7.6 (1H); 7.39, 7.42 (d, 1H); 7.25 (1H); 6.07 (1H); 3.86 (3H); 3.70 (3H); 3.63 (3H); 3.05 (3H) ppm.

EXAMPLE II-4

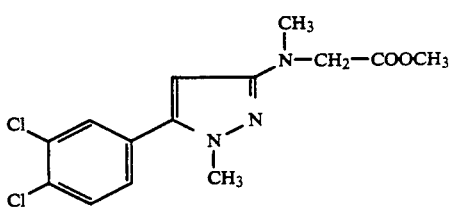

To 81 g (0.3 mol) of 3.4-dichlorophenyl 2,2-dichlorovinyl ketone (cf. Synthesis 1982, 204) in 300 ml of tetrahydrofuran there is added dropwise with stirring at room temperature a mixture of 30.3 g (0.3 mol) of triethylamine and 30.9 g (0.3 mol) of methyl sarcosinate, and the mixture is subsequently stirred for 16 hours at room temperature. After this, 13.8 g (0.3 mol) of methylhydrazine and a further 30.3 g (0.3 mol) of triethylamine are added, the mixture is stirred for one hour at 60° C., precipitated salt is filtered off, the filtrate is concentrated in vacuo, and the residue is chromatographed on silica gel (eluent: dichloromethane).

53.1 g (54% of theory) of methyl N-[5-(3,4-dichlorophenyl)-1-methylpyrazol-3-yl]-N-methylamino-acetate are obtained as an oil.

$^1$H NMR (CDCl$_3$/tetramethylsilane): $\delta$=2.88 (3H); 3.75 (5H); 3.79 (3H); 6.18 (1H); 7.4–7.45 (1H); 7.5–7.6 (1H); 7.84 (1H) ppm.

EXAMPLE 5

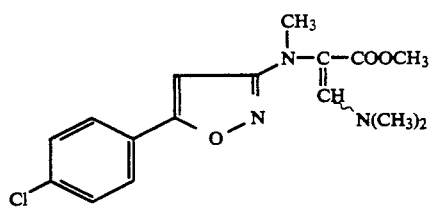

9.5 g (0.034 mol) of methyl N-[5-(4-chlorophenyl)isoxazol-3-yl]-N-methylaminoacetate together with 9.1 g (0.052 mol) of t-butoxy-bis-(dimethylamino)-methane are heated for one hour at a bath temperature of 100° C. For working-up, the mixture is concentrated under a water pump vacuum, and the residue is recrystallised from chloroform/toluene (8:3).

8.5 g (75% of theory) of methyl 2-{N-[5-(4-chlorophenyl)isoxazol-3-yl]-N-methylamino}-3-dimethylaminoacrylate of melting point 190° C. are obtained.

EXAMPLE V-5

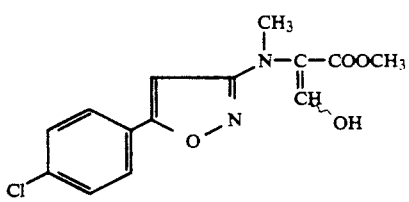

5 g (0.0149 mol) of methyl 2-{N-[5-(4-chlorophenyl)isoxazol-3-yl]-N-methylamino}-3-dimethylaminoacrylate and 15 ml (0.015 mol) of 1-normal hydrochloric acid are stirred for 2 hours at room temperature in 20 ml of dimethylformamide, water is subsequently added, the mixture is extracted using dichloromethane, and the organic phases are dried over sodium sulphate and concentrated in vacuo.

4.1 g (89% of theory) of methyl 2-{N-[5-(4-chlorophenyl)isoxazol-3-yl]-N-methylamino}-3-hydroxyacrylate are obtained as an oily crude product which can be employed in the next step without further purification.

EXAMPLE II-5

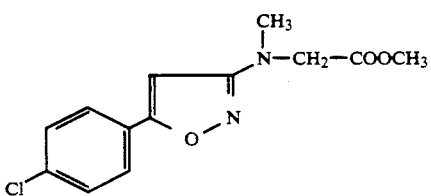

To 23.6 g (0.1 mol) of 4-chlorophenyl 2,2-dichlorovinyl ketone (cf. Synthesis 1982, 204) in 100 ml of tetrahydrofuran there is added dropwise with stirring at 20° C. a mixture of 10.3 g (0.1 mol) of methyl sarcosinate and 10.1 g (0.1 mol) of triethylamine, the mixture is stirred for one hour at room temperature, precipitated salt is filtered off, and the filtrate is poured into a mixture of 16 g (0.23 mol) of hydroxylamine hydrochloride and 200 ml of pyridine. The mixture is stirred for one hour at 80° C., a little toluene is added, toluene and pyridine are distilled off together, the residue is partitioned between dichloromethane and water, the organic phase is separated off, dried over sodium sulphate and concentrated in vacuo, and the residue is recrystallised from 450 ml of methanol.

13.9 g (50% of theory) of methyl N-[5-(4-chlorophenyl)isoxazol-3-yl]-N-methylamino-acetate of melting point 141° C. are obtained.

EXAMPLE 6

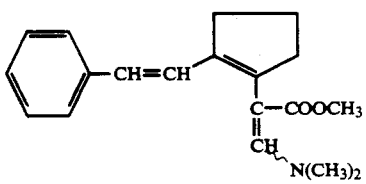

To 9.5 g (0.039 mol) of methyl 2-[2-(2-phenylethenyl)-1-cyclopentenyl]-acetate (cf. DE-OS (German Published Specification) 3,928,999) in 40 ml of low-boiling petroleum ether there are added dropwise with stirring at room temperature 9.5 g (0.054 mol) of t-butoxy-bis(dimethylamino)-methane, and the mixture is subsequently stirred for a further 12 hours at room temperature. For working-up, precipitated product is filtered off with suction and dried.

8.5 g (73% of theory) of methyl 2-[2-(2-phenylethenyl)-1-cyclopentenyl]-3-dimethylaminoacrylate are obtained as an oil.

$^1$H NMR (CDCl$_3$/tetramethylsilane):

δ=7.56 (1H); 7.12-7.42 m (5H); 6.80, 6.85 d (1H); 6.38, 6.43 d (1H); 3.66 (3H); 2.83 (6H); 2.5-3.0 m (4H); 2.8-2.08 (2H) ppm.

EXAMPLE V-6

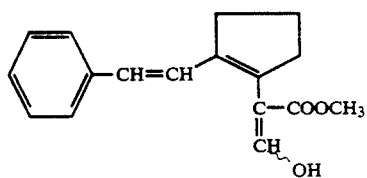

To 8.5 g (0.0286 mol) of methyl 2-[2-(2-phenylethenyl)-1-cyclopentenyl]-3-dimethylaminoacrylate in 38 ml of dimethylformamide there are added dropwise with stirring 25 ml of 2-normal hydrochloric acid, the mixture is subsequently stirred for 1 hour at room temperature, then diluted with water, and extracted with diethyl ether. The combined ether phases are dried over sodium sulphate and concentrated in vacuo.

7.1 g (92% of theory) of methyl 2-[2-(2-phenylethenyl)-1-cyclopentenyl]-3-hydroxyacrylate are obtained as an oil which can be employed in the next step without further purification.

$^1$H NMR (CDCl$_3$/tetramethylsilane):

δ=12.0 d (1H); 7.03-7.45 m (5H); 6.93, 6.99 d (1H); 6.45, 6.51 d (1H); 3.79 (3H); 2.55-2.75 m (4H); 1.85-2.05 m (2H) ppm.

EXAMPLE IV-6

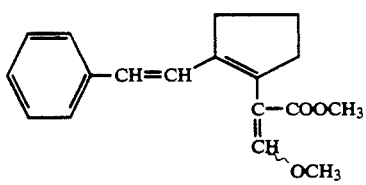

To 7.1 g (0.026 mol) of methyl 2-[2-(2-phenylethenyl)-1-cyclopentenyl]-3-hydroxyacrylate and 7.3 g (0.053 mol) of potassium carbonate in 30 ml of dimethylformamide there are added dropwise at 0° C. with stirring 3.3 g (0.026 mol) of dimethyl sulphate, the reaction mixture is subsequently stirred for 15 hours at room temperature, and then poured into water and extracted using diethyl ether, the combined organic phases are dried over sodium sulphate and evaporated in vacuo, and the residue is recrystallised from toluene.

4.6 g (62% of theory) of methyl 2-[2-(2-phenylethenyl)-1-cyclopentenyl]-3-methoxy-acrylate of melting point 123°-125 C. are obtained.

EXAMPLE 7

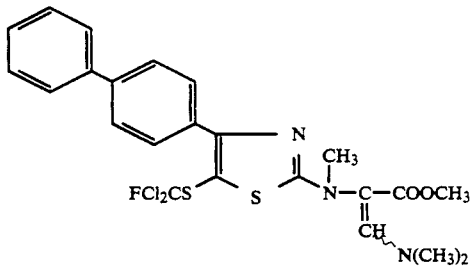

A mixture of 6.0 g (0.013 mol) of methyl N-[5-dichlorofluoromethylthio-4-(4-phenyl)-phenylthiazol-2-yl]-N-methylamino-acetate and 20 g (0.124 mol) of t-butoxybis-(dimethylamino)-methane is heated for 10 hours at 100° C. and subsequently cooled and treated with 200 ml of water and 200 ml of ethyl acetate. The ethyl acetate phase is separated off, dried and concentrated.

6.2 g (91% of theory) of methyl 2-{N-(5-dichlorofluoromethylthio-4-(4-phenyl)-phenylthiazol-2-yl]-N-methylamino}-3-dimethylaminoacrylate are obtained as an oil.

$^1$H NMR (DMSO-d$_6$/tetramethylsilane):

δ=3.25 (3H; N—CH$_3$); 3.60 (3H; COOCH$_3$); 3.34 (6H; N(CH$_3$)$_2$) ppm.

EXAMPLE IV-7

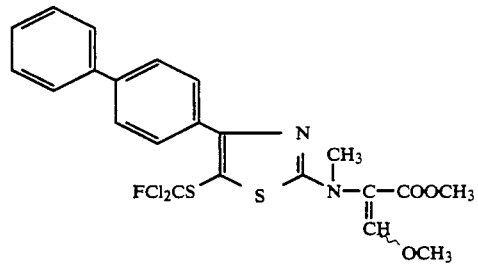

To 5.8 g (0.011 mol) of methyl 2-{N-[5-dichlorofluoromethylthio-4-(4-phenyl)-phenylthiazol-2-yl]-N-methyl-amino}-3-dimethylaminoacrylate in 200 ml of dimethylformamide there are added 2.5 ml (0.025 mol) of concentrated hydrochloric acid, the mixture is heated for 3 hours at 60° C. and then cooled, 6.9 g (0.05 mol) of potassium carbonate and 6.3 g (0.05 mol) of dimethyl sulphate are added, the reaction mixture is stirred for 12 hours at room temperature and subsequently poured into water, the mixture is extracted using dichloromethane, the organic phase is dried over sodium sulphate and concentrated in vacuo, and the residue is chromatographed on silica gel (eluent: dichloromethane).

3.2 g (60% of theory) of methyl 2-{N-[5-dichlorofluoromethylthio-4-(4-phenyl)-phenylthiazol-2-yl]-N-methylamino}-3-methoxyacrylate are obtained as an oil.

$^1$H NMR (CDCl$_3$/tetramethylsilane):

δ=3.34 (3H; N—CH$_3$); 3.37 (3H; COOCH$_3$); 3.78 (3H; OCH$_3$) ppm.

EXAMPLE 8

403 g (1.386 mol) of methyl N-[6-(4-chlorophenyl)-2-pyridyl]-N-methylaminoacetate and 981.4 g (5.63 mol) of t-butoxy-bis-(dimethylamino)-methane are stirred for 25 hours at 60° C. and subsequently concentrated in vacuo, the residue is treated with 3 l of dichloromethane, the mixture is washed three times with 500 ml portions of water, dried over magnesium sulphate and concentrated in vacuo, the residue is stirred with 2 l of petroleum ether, filtered off with suction, rinsed with 1 l of petroleum ether and dried in the air.

452 g (89% of theory) of methyl 2-{N-[6-(4-chlorophenyl)-2-pyridyl]-N-methylamino}-3-dimethylaminoacrylate of melting point 101° C. are obtained.

EXAMPLE IV-8

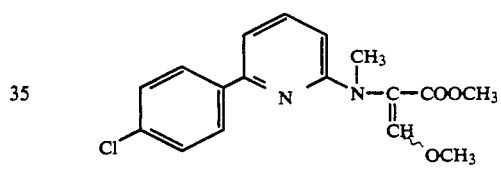

400 g (1.16 mol) of methyl 2-{N-[6-(4-chlorophenyl)-2-pyridyl]-N-methylamino}-3-dimethylaminoacrylate, 1158 ml of 2-normal hydrochloric acid and 1158 ml of water in 4 l of dimethylformamide are stirred for 2 hours at 60° C., the mixture is allowed to cool to 20° C. and then stirred into 15 l of water and 250 g of sodium hydrogen carbonate, precipitated product is filtered off with suction and dissolved in 2 l of dichloromethane, and the mixture is washed three times with 1 l portions of water, dried over magnesium sulphate and concentrated in vacuo. The residue is dissolved in 4 l of dimethylformamide, and the solution is treated with 320 g (2.3 mol) of potassium carbonate, stirred for 30 minutes at room temperature, treated dropwise with 178 g (1.4 mol) of dimethyl sulphate, with cooling, and stirred into 15 l of water, and the mixture is extracted twice using 1 l portions of dichloromethane, and the dichloromethane phases are washed twice using 500 ml portions of water, dried over magnesium sulphate and evaporated in vacuo. The residue is recrystallised from 600 ml of t-amyl methyl ether and dried in vacuo at 40° C.

270 g (70% of theory) of methyl 2-{N-[6-(4-chlorophenyl)-2-pyridyl]-N-methylamino}-3-methoxyacrylate of melting point 135° C. are obtained.

EXAMPLE II-8

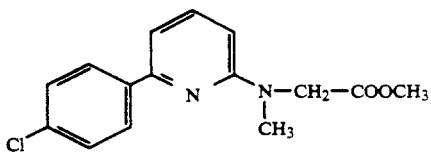

123 g (0.444 mol) of N-[6-(4-chlorophenyl)-2-pyridyl]-N-methylaminoacetic acid and 1 ml of concentrated sulphuric acid are refluxed for 16 hours in 750 ml of methanol and subsequently concentrated in vacuo, the residue is dissolved in 500 ml of dichloromethane, the solution is washed once with 250 ml of 3% strength aqueous sodium hydroxide solution and washed three times with 100 ml portions of water, dried over magnesium sulphate and concentrated in vacuo, and the residue is stirred with 500 ml of petroleum ether, filtered off with suction and dried.

92 g (71% of theory) of methyl N-[6-(4-chlorophenyl)-2-pyridyl]-N-methylaminoacetate of melting point 54° C. are obtained.

EXAMPLE 9

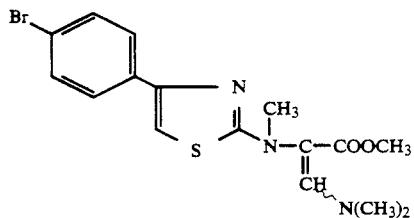

17 g (0.04982 mol) of methyl N-[4-(4-bromophenyl)-2-thiazolyl]-N-methylamino-acetate and 17.4 g (0.1078 mol) of t-butoxy-bis-(dimethylamino)-methane are stirred for 6 hours at 100° C., the mixture is cooled, treated with ice-water and stirred for a few hours at room temperature, and precipitated crystals are filtered off with suction and dried. 17.5 g (89% of theory) of methyl 2-{N-[4-(4-bromophenyl)-2-thiazolyl]-N-methylamino}-3-dimethylaminoacrylate of melting point 184°-185° C. are obtained.

EXAMPLE 10

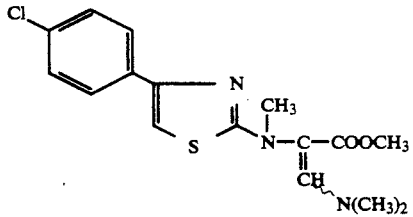

3.75 g (0.00998 mol) of methyl N-[5-bromo-4-(4-chlorophenyl)-2-thiazolyl]-N-methylamino-acetate and 3.5 g (0.02168 mol) of t-butoxy-bis-(dimethylamino)-methane in 10 ml of dioxane are stirred for 15 hours at reflux temperature, the mixture is cooled, treated with water and dichloromethane and stirred for 2 hours at room temperature, and the organic phase is separated off, dried over magnesium sulphate and concentrated in vacuo.

4.1 g (95% of theory) of methyl 2-{N-[5-bromo-4-(4-chlorophenyl)-2-thiazolyl]-N-methylamino}-3-dimethylaminoacrylate are obtained as an oil.

$^1$H NMR (CDCl$_3$/tetramethylsilane):

δ=3.24 (3H; N—C$\underline{H}_3$); 3.69 (3H; COOC$\underline{H}_3$); 3.70 (6H; N(C$\underline{H}_3$)$_2$) ppm.

Comparison Experiment A (cf. Preparation Example 2)

To a mixture of 1.2 g (0.05 mol) of sodium hydride in 30 ml of dimethylformamide there is added a solution of 5.2 g (0.021 mol) of methyl N-(6-bromo-2-pyridyl)N-methylaminoacetate and 30 g (0.72 mol) of methyl formate in 30 ml of dimethylformamide, the mixture is subsequently stirred for 15 hours at room temperature, 12.5 g (0.1 mol) of dimethyl sulphate are then added, the mixture is stirred for a further 15 hours at room temperature and then poured into water, extracted using ethyl acetate, dried over magnesium sulphate and concentrated in vacuo, and the residue is chromatographed on silica gel (eluent: dichloromethane/n-hexane 5:1).

1.5 g (29% of theory) of the starting material methyl N-(6-bromo-2-pyridyl)-N-methylaminoacetate are obtained as the 1st fraction and 1.8 g (30% of theory) of methyl 2-[N-(6-bromo-2-pyridyl)-N-methylamino]-3-methoxyacrylate of melting point 78°-79° C. as the 2nd fraction.

Comparison Experiment B (cf. Preparation Example 2)

2.6 g (0.01 mol) of methyl N-(6-bromo-2-pyridyl)-N-methylaminoacetate and 2.4 g (0.02 mol) of dimethylformamide dimethyl acetal, either dissolved in 5 ml of toluene or without the addition of a diluent, were stirred for 15 hours at reflux temperature. In both cases, examination of the reaction mixtures by thin-layer chromatography showed only traces of the desired reaction product methyl 2-[N-(6-bromo-2-pyridyl)-N-methylamino]-3-methoxyacrylate.

Comparison Experiment C (cf. Preparation Example 7)

6.45 g (0.015 mol) of methyl N-[5-dichlorofluoromethylthio-4-(4-phenyl)-phenyl-2-thiazolyl]-N-methylaminoacetate and 20 g (0.48 mol) of methyl formate in 10 mol of dimethylformamide are added dropwise at 0° C. to 1 g (0.033 mol) of sodium hydride in 10 ml of dimethylformamide, with stirring. The reaction mixture is subsequently stirred for 15 hours at room temperature, 4.0 g (0.032 mol) of dimethyl sulphate are then added, the reaction mixture is stirred for a further 3 hours at room temperature and then poured into water, and the mixture is extracted using ethyl acetate, dried over sodium sulphate and concentrated in vacuo.

The residue contains only traces of the desired compound methyl 2-{N-[5-dichlorofluoromethylthio-4-(4-phenyl)-phenyl-2-thiazolyl]-N-methylamino}-3-methoxyacrylate.

Comparison Experiment D (cf. Preparation Example 8)

To 2.4 g (0.1 mol) of sodium hydride in 60 ml of dimethylformamide there are added dropwise at room temperature 10.3 g (0.035 mol) of methyl N-[6-(4-chlorophenyl)-2-pyridyl]-N-methylaminoacetate and 50 g (1.2 mol) of methyl formate in 50 ml of dimethylformamide, with stirring, and the mixture is subsequently stirred for 3 days at room temperature, a further 0.5 g (0.021 mol) of sodium hydride and 10 g (0.24 mol) of methyl formate are added, the mixture is stirred for a further 5 hours at room temperature, another 0.5 g (0.021 mol) of sodium hydride and 10 g (0.24 mol) of methyl formate are then added, and the mixture is stirred for a further 24 hours at room temperature.

14.0 g (0.11 mol) of dimethyl sulphate are then added, and the mixture is stirred for a further 48 hours at room temperature. For working-up, the reaction mixture is poured into water, extracted using ethyl acetate, dried over magnesium sulphate and concentrated in vacuo, and the residue is chromatographed on silica gel (eluent: dichloromethane/n-hexane 5:1).

7.1 g (69% of theory) of the starting compound methyl N-[6-(4-chlorophenyl)-2-pyridyl]-N-methylaminoacetate are obtained as the 1st fraction and 0.5 g (4.2% of theory) of the desired product methyl 2-{N-[6-(4-chlorophenyl)-2-pyridyl]-N-methylamino}-3-methoxyacrylate of melting point 120° C. as the 2nd fraction.

We claim:

1. Process for the preparation of 3-aminocrylic esters of the general formula (I)

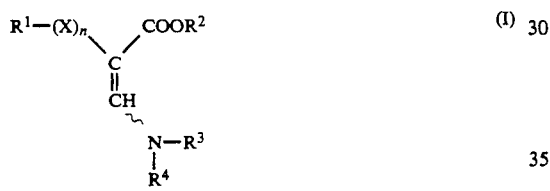

in which
R$^1$ represents a carbo- or heterocycle, each of which is optionally substituted, wherein the heterocycle is:

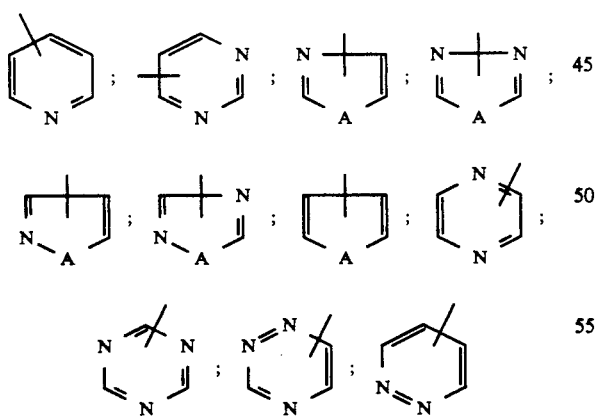

which are optionally benzo-fused and in which A represents oxygen, sulphur or an NH group, suitable substituents in each case being halogen, cyano, nitro, in each case straight-chain or branched alkyl, alkoxy or alkylthio, each of which has 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl, alkoximinoalkyl, dialkylamino or dialkylaminocarbonyl, each of which has 1 to 4 carbon atoms in the individual alkyl moieties, in each case straight-chain or branched alkenyl or alkynyl, each of which has 2 to 8 carbon atoms, cycloalkyl having 3 to 7 carbon atoms, divalent alkanediyl having 3 to 5 carbon atoms, or aryl, aryloxy, arylthio, arylcarbonyl, aralkyl, aralkenyl, aralkinyl, aralkyloxy, aralkythio, heteroarylalkyl, heteroarylalkenyl, heteroaryloxy, heteroarylthio, heteroarylcarbonyl, heteroarylalkyloxy, heteroarylalkylthio or heteroaryl, each of which has 6 to 10 carbon atoms in the aryl moiety or 2 to 9 carbon atoms and 1 to 4 identical or different hetero atoms selected from nitrogen, oxygen or sulphur—in the heteroaryl moiety and if appropriate 1 to 6 carbon atoms in the straight-chain or branched alkyl moiety or if appropriate 2 to 6 carbon atoms in the straight-chain or branched alkenyl moiety or alkinyl moiety, each of which is optionally monosubstituted or polysubstituted in the aryl moiety or in the heteroaryl moiety by identical or different substituents from the series comprising halogen, alkyl, alkoxy, alkylthio, halogenoalkyl, halogenoalkoxy, halogenoalkylthio, dioxyalkylene, halogen-substituted dioxyalkylene or optionally substituted phenyl;

R$^2$ represents optionally substituted alkyl,

R$^3$ and R$^4$ either independently of one another in each case represent optionally substituted alkyl, or together with the nitrogen atom to which they are bonded represent a 1-pyrrolidinyl, 1-piperidinyl or 4-morpholinyl radical, X represents oxygen, sulphur or one of the radicals

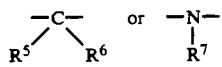

and n represents a number 0 or 1, where

R$^5$, R$^6$ and R$^7$ independently of one another in each case represent hydrogen or represent alkyl or alkenyl, each of which is optionally substituted, characterised in that substituted acetic esters of the formula (II)

$$R^1-(X)_n-CH_2-COOR^2 \qquad (II)$$

in which

R$^1$, R$^2$, X and n have the abovementioned meaning, are reacted with orthoformic acid diamide esters of the formula (III)

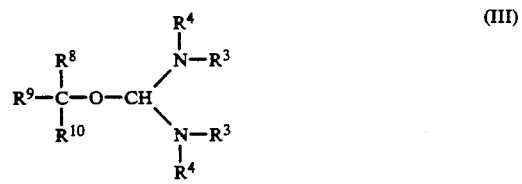

in which

R$^8$ represents hydrogen or alkyl,

R$^9$ and R$^{10}$ either independently of one another in each case represent alkyl, or together with the carbon atom to which they are bonded represent a cycloalkyl radical, and $R^3$ and $R^4$ have the abovementioned meaning, optionally in the presence of a diluent.

2. Process according to claim 1, characterised in that compounds of the formula (I) are prepared in which $R^1$ represents a carbocycle which has 5 to 10 carbon atoms and which is optionally monosubstituted or polysubstitued by identical or different substituents, saturated, monounsaturated or polyunsaturated or aromatic, or represents a heterocycle according to claim 1 which is optionally monosubstituted or polysubstituted by identical or different substituents, saturated, monounsaturated or polyunsaturated or aromatic in each case being:

halogen, cyano, nitro, in each case straight-chain or branched alkyl, alkoxy or alkylthio, each of which has 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl, alkoxyiminoalkyl, dialkylamino or dialkylaminocarbonyl, each of which has 1 to 4 carbon atoms in the individual alkyl moieties, in each case straight-chain or branched alkenyl or alkynyl, each of which has 2 to 8 carbon atoms, cycloalkyl having 3 to 7 carbon atoms, divalent alkanediyl having 3 to 5 carbon atoms, or aryl, aryloxy, arylthio, arylcarbonyl, aralkyl, aralkenyl, aralkinyl, aralkyloxy, aralkylthio, heteroarylalkyl, heteroarylalkenyl, heteroaryloxy, heteroarylthio, heteroarylcarbonyl, heteroarylalkyloxy, heteroarylalkylthio or heteroaryl, each of which has 6 to 10 carbon atoms in the aryl moiety or 2 to 9 carbon atoms and 1 to 4 identical or different hetero atoms selected from nitrogen, oxygen or sulphur—in the heteroaryl moiety and if appropriate 1 to 6 carbon atoms in the straight-chain or branched alkyl moiety or if appropriate 2 to 6 carbon atoms in the straight-chain or branched alkenyl moiety or alkinyl moiety, each of which is optionally monosubstituted or polysubstituted in the aryl moiety or in the heteroaryl moiety by identical or different substituents from the series comprising halogen, alkyl, alkoxy, alkylthio, halogenoalkyl, halogenoalkoxy, halogenoalkylthio, dioxyalkylene, halogen-substituted dioxyalkylene or optionally substituted phenyl;

$R^2$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted or polysubstituted in the aryl moiety by identical or different substituents, suitable aryl substituents being: halogen, cyano, nitro, in each case straight-chain or branched alkyl, alkoxy or alkylthio, each of which has 1 to to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, or aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which as 1 to 4 carbon atoms and if appropriate 1 to 9 identical or different halogen atoms, or heteroarylalkyl or heteroaryl, each of which has 2 to 0 carbon atoms and 1 to 4 identical or different hetero atoms, selected from nitrogen, oxygen or sulphur—in the heteroaryl moiety and if appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms;

$R^3$ and $R^4$ either independently of one another in each case represent straight-chain or branched alkyl having 1 to 6 carbon atoms, or together with the nitrogen atom to which they are bonded represent a saturated 5- to 7-membered heterocycle which is a 1-pyrrolidinyl, 1-piperidinyl or 4-morpholinyl radical, and which is optionally monosubstituted or polysubstituted by identical or different straight-chain or branched alkyl radicals having 1 to 4 carbon atoms, X represents oxygen, sulphur or one of the radicals

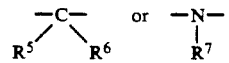

and n represent a number 0 or 1 where $R^5$, $R^6$ and $R^7$ independently of one another represent hydrogen, straight-chain or branched alkyl having 1 to 6 carbon atoms or alkenyl having 2 to 6 carbon atoms, or represent aralkyl which has 1 to 6 carbon atoms in the straight-chain or branched alkyl moiety and 6 to 10 carbon atoms in the aryl moiety or aralkenyl which has 2 to 6 carbon atoms in the straight-chain or branched alkenyl moiety and 6 to 10 carbon atoms in the aryl moiety, each of these aralkyl or aralkenyl radicals optionally being monosubstituted or polysubstituted in the aryl moiety by identical or different substituents, suitable aryl substituents in each case being those mentioned in the case of $R^2$.

3. Process according to claim 1, characterised in that it is carried out at temperatures from $-35°$ C. to $+150°$ C.

4. Process according to claim 1, characterised in that 1.0 to 15.0 moles of orthoformic acid diamide ester of the formula (III) are employed per mole of substituted acetic ester of the formula (II).

5. Process according to claim 1, characterised in that orthoformic acid diamide esters of the formula (III) are employed in which $R^3$ and $R^4$ have the meaning given in claim 2 and $R^8$ represents hydrogen or straight-chain or branched alkyl having 1 to 4 carbon atoms, and $R^9$ and $R^{10}$ independently of one another in each case represent straight-chain or branched alkyl having 1 to 4 carbon atoms, or together with the carbon atom to which they are bonded represent cycloalkyl having 5 to 7 carbon atoms.

* * * * *

UNITED STATES PATENT AND TRADEMARK OFFICE
CERTIFICATE OF CORRECTION

PATENT NO. : 5,196,541
DATED : March 23, 1993
INVENTOR(S) : Gayer, et al.

It is certified that error appears in the above-identified patent and that said Letters Patent is hereby corrected as shown below:

Col. 20, line 10    Delete " aralkythio " and substitute -- aralkylthio --

Col. 22, line 9     Delete " 0 carbon " and substitute -- 9 carbon --

Signed and Sealed this

Twentieth Day of September, 1994

Attest:

BRUCE LEHMAN

*Attesting Officer*    *Commissioner of Patents and Trademarks*